US007820796B2

(12) United States Patent
Booth et al.

(10) Patent No.: US 7,820,796 B2
(45) Date of Patent: *Oct. 26, 2010

(54) METHODS FOR PRODUCING FACTOR VIII PROTEINS

(75) Inventors: James Booth, Andover, MA (US); Suresh Vunnum, Burlington, MA (US); Brian D. Kelley, Medford, MA (US)

(73) Assignee: Genetics Institute, LLC., Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 11/043,784

(22) Filed: Jan. 26, 2005

(65) Prior Publication Data

US 2005/0165221 A1 Jul. 28, 2005

Related U.S. Application Data

(63) Continuation-in-part of application No. 10/728,242, filed on Dec. 3, 2003, now abandoned, which is a continuation of application No. 09/752,280, filed on Dec. 29, 2000, now Pat. No. 6,683,159, which is a continuation of application No. 09/266,322, filed on Mar. 11, 1999, now abandoned.

(60) Provisional application No. 60/077,802, filed on Mar. 12, 1998.

(51) Int. Cl.
*C07K 14/755* (2006.01)
*C07K 1/18* (2006.01)
*C07K 1/22* (2006.01)

(52) U.S. Cl. .................. 530/383; 530/380; 530/413; 530/415; 530/426; 530/350; 514/2; 514/12

(58) Field of Classification Search .......... 514/2, 514/12; 530/350, 380, 383, 413, 414, 415, 530/416
See application file for complete search history.

(56) References Cited

U.S. PATENT DOCUMENTS

| | | | | |
|---|---|---|---|---|
| 4,312,935 A | * | 1/1982 | Engler et al. | 430/296 |
| 4,486,602 A | * | 12/1984 | Horii et al. | 564/360 |
| 4,757,006 A | | 7/1988 | Toole et al. | |
| 4,868,112 A | | 9/1989 | Toole, Jr. | |
| 5,470,954 A | | 11/1995 | Neslund et al. | |
| 6,197,526 B1 | * | 3/2001 | Yu et al. | 435/7.1 |
| 6,197,596 B1 | | 3/2001 | Newkirk | |
| 6,683,159 B2 | | 1/2004 | Kelley et al. | |

FOREIGN PATENT DOCUMENTS

| | | |
|---|---|---|
| EP | 0 786 474 A1 | 7/1997 |
| WO | WO 86/04486 | 8/1986 |
| WO | WO 86/06101 | 10/1986 |
| WO | WO 87/04187 | 7/1987 |
| WO | WO 87/07144 | 12/1987 |
| WO | WO 88/03558 | 5/1988 |
| WO | WO 88/08035 | 10/1988 |

OTHER PUBLICATIONS

U.S. Appl. No. 10/728,242, filed Dec. 3, 2003, Kelley et al.
J. Toole et al., "Molecular Cloning of a cDNA Encoding Human Antihaemophilic Factor," Nature, 312:342-347 (1984).
Wood et al., "Expression of Active Human Factor VIII from Recombinant DNA Clones," Nature, 312:330-337 (1984).
D.N. Fass, et al., "Monoclonal Antibodies to Procine Factor VIII Coagulant and Their Use in the Isolation of Active Coagulant Protein," Blood, 59:594-600 (1982).
Vehar, Gordon A., et al., "Structure of human factor VIII,", Nature, 312:337-342 (1984).
Fass, D.N., et al., "Monoclonal Antibodies to Porcine Factor VIII Coagulant and Their Use in the Isolation of Active Coagulant Protein," Blood, 59:594-600 (1982).
Toole, J.J., et al., "Exploration of Structure-Function Relationships in Human Factor VIII by Site-directed Mutagenesis;," Cold Spring Harbor Symposium on Quantitative Biology, vol. LI. © 1986 Cold Spring Harbor Laboratory 0-87969-052-6/86.
Wood, William I., et al., "Expression of active human factor VIII from recombinant DNA clones," Nature, 312:330-337 (1984).
Kelley et al., "Development and Validation of an Affinity Chromatography Step Using a Peptide Ligand for cGMP Production of Factor VIII," Biotechnology and Bioengineering, 87(3):400-412 (2004).
Kelley et al., "Isolation of a peptide ligand for affinity purification of factor VIII using phage display," Journal of Chromatography A, 1038:121-130 (2004).

* cited by examiner

*Primary Examiner*—Chih-Min Kam
(74) *Attorney, Agent, or Firm*—Wilmer Cutler Pickering Hale and Dorr LLP

(57) ABSTRACT

Methods are provided for purification of Factor VIII polypeptides by affinity chromatography and ion exchange chromatography, in which the eluate from the affinity column is diluted with a solution comprising higher salt concentration, or lower non-polar agent concentration than that of the elution solution, prior to passing the diluted solution through the ion exchange column. The affinity matrix may comprise a monoclonal antibody or a peptide ligand. The methods result in improved purification without significant yield loss.

62 Claims, No Drawings

METHODS FOR PRODUCING FACTOR VIII PROTEINS

CROSS-REFERENCE TO RELATED APPLICATIONS

This application is a Continuation-in-part of application Ser. No. 10/728,242, filed on Dec. 3, 2003, now abandoned, which application is a Continuation of application Ser. No. 09/752,280, filed Dec. 29, 2000, now U.S. Pat. No. 6,683,159, which application is a Continuation of application Ser. No. 09/266,322, filed on Mar. 11, 1999, now abandoned, which application claims priority from Provisional Application No. 60/077,802, filed on Mar. 12, 1998.

FIELD OF THE INVENTION

The present invention relates to improved methods for the purification of procoagulant proteins, particularly recombinant production of Factor VIII and related proteins.

BACKGROUND OF THE INVENTION

Hemophilia is an inherited disease which has been known for centuries, but it is only within the last few decades that it has been possible to differentiate among the various forms; hemophilia A and hemophilia B. Hemophilia A is caused by strongly decreased level or absence of biologically active coagulation factor VIII, which is a protein normally present in plasma.

Factor VIII (FVIII) is a large and complex glycoprotein that participates in the blood coagulation cascade. Deficiencies in FVIII production in vivo caused by genetic mutation can cause hemophilia, which is treated by infusion of purified preparations of human FVIII (Lee, *Thromb Haemost,* 82:516-524, 1999). The first purified FVIII products were derived from human serum, isolated from the cryoprecipitate from the Cohn fractionation process.

Research efforts have focused on the development of methods for creating and isolating highly purified, biologically active factor VIII in full-length and derivative forms. Advantages of a highly purified protein include reduced levels of extraneous proteins in the therapeutic mix as well as a decreased likelihood of the presence of infectious agents. A more purified form of factor VIII may also be administered in smaller doses, possibly reducing the risk of developing anti-factor VIII antibodies, as lower doses would be less challenging to the immune system.

Significant steps have been taken toward the recombinant production of factor VIII beginning with the isolation of biologically active factor VIII fragments. See, U.S. Pat. No. 4,749,780; U.S. Pat. No. 4,877,614. The gene encoding the full-length human factor VIII protein was isolated by taking advantage of its sequence homology with porcine factor VIII. See, U.S. Pat. No. 4,757,006. DNA sequences encoding the human coagulation cofactor, Factor VIII:C (FVIII), are also known in the art [see, e.g., Toole et al., *Nature* 312:312-317, 1984; Wood et al., *Nature* 312:330-337, 1984; Vehar et al.; *Nature* 312:337-342, 1984], as well as methods for expressing them to produce recombinant FVIII [see e.g. Toole, U.S. Pat. No. 4,757,006; WO 87/04187, WO 88/08035 and WO 88/03558]. The expression of human and porcine protein having factor VIII:C procoagulant activity was also described in U.S. Pat. No. 4,575,006. Active variants and analogs of FVIII protein, and DNA sequences encoding them, have also been reported [see, e.g. Toole, U.S. Pat. No. 4,868,112; EP 0 786 474; WO 86/06101 and WO 87/07144]. Generally, such variants and analogs are modified such that part or all of the B domain is missing and/or specific amino acid positions are modified, for example, such that normally protease-labile sites are resistant to proteolysis, e.g., by thrombin or activated Protein C. Other analogs include modification at one or more lysine and/or tyrosine residues.

Since severe side effects involving the production of anti-factor VIII antibodies exist with the administration of the protein isolated from both human and non-human sources, truncated lower molecular weight proteins exhibiting procoagulant activity have been designed. U.S. Pat. No. 4,868,112 reports an alternative method of treatment with lower molecular weight porcine factor VIII of approximately 2000 amino acids exhibiting similar procoagulant activity as full-length factor VIII. The removal of certain amino acids and up to 19 of the 25 possible glycosylation sites reduced the antigenicity of the protein and thereby the likelihood of developing anti-factor VIII antibodies. However, one difficulty with the development of recombinant factor VIII is achieving production levels in sufficiently high yields.

Various Factor VIII cDNA molecules coding for recombinant factor VIII derivatives have been developed. For example, U.S. Pat. No. 5,661,008 ("the '008 patent") describes a modified factor VIII derived from a full-length factor VIII cDNA that, when expressed in animal cells, produced high levels of a factor VIII-like protein with factor VIII activity. The protein consisted essentially of two polypeptide chains derived from human factor VIII, the chains having molecular weights of 90 kDa and 80 kDa, respectively. The final active protein is made up of amino acids 1 to 743 and 1638 through 2332 of human factor VIII, the description of which is incorporated by reference herein in its entirety. This polypeptide sequence is commercially known as rFVIII-SQ or REFACTO®. See also, Lind et al., *Euro. J. Biochem.,* 232:19-27 (1995); Sandberg et al., *Sem Hematol,* 38 (Suppl 4):4-12, 2001.

Other forms of truncated FVIII can also be constructed in which the B-domain is generally deleted. In such embodiments, the amino acids of the heavy chain, consisting essentially of amino acids 1 through 740 of human Factor VIII and having a molecular weight of approximately 90 kD are connected to the amino acids of the light chain, consisting essentially of amino acids 1649 to 2332 of human Factor VIII and having a molecular weight of approximately 80 kD. The heavy and light chains may be connected by a linker peptide of from 2 to 15 amino acids, for example a linker comprising lysine or arginine residues, or alternatively, linked by a metal ion bond.

Affinity chromatography offers a powerful method for protein purification, with the potential to provide exquisite selectivity from contaminating proteins based on the unique interaction between the target protein and ligand immobilized on the resin (Carlsson et al., Affinity chromatography. In: *Protein purification: Principles, high resolution methods, and applications.* Editors Janson J-C, and Ryden L, New York, Wiley-Liss p 375-442, 1998; Harakas, Biospecific affinity chromatography. In: *Protein purification process engineering.* Editor Harrison R G, New York, Marcel Dekker p 259-316, 1994). Development of an affinity chromatography step can be difficult if a ligand with suitable affinity or selectivity cannot be identified, or if the elution of the product cannot be achieved without resorting to extreme conditions that may be harmful to the product. While small chemical ligands can be used for affinity separations, their utility has traditionally been restricted to cases where they act as a substrate analog, competitive inhibitor, or co-factor for purification of an enzyme. However, recent work with combinatorial libraries has expanded the repertoire for small molecule ligands (Lowe, *Curr Op Chem Biol*, 5:248-256, 2001; Morrill, *J Chrom B*, 774:1-15, 2002). Often, the strength of this binding interaction is moderate to weak (dissociation constants in the millimolar to micromolar range).

At the other extreme, monoclonal antibodies (Mabs) are used as affinity ligands, and often have very high binding affinities (dissociation constants in the nanomolar range) that are difficult to disrupt without extreme pH or high levels of solvents or chaotropes (Goding, Affinity chromatography. In: *Monoclonal antibodies: principles and practice*. London: Academic Press, p 327-351, 1986). Affinity peptides can be thought of as intermediate between these two cases, as they offer the potential for enormous diversity in chemical properties, and hence selectivity. Further, by using combinatorial methods based on either biological or chemical systems to generate large libraries of unique peptides (Buettner et al., *Int J Peptide Protein Res*, 47:70-83, 1996; Kaufman et al., *Biotechnol Biogen*, 77:278-289, 2002; Ladner, *Trends Biotechnol*, 13:426-430, 1995; Sato et al., *Biotechnol Prog* 18:182-192, 2002), sequences may be identified with moderate binding affinities that are sufficient to capture the product without undue losses, but which are still capable of eluting the bound protein under mild conditions.

Peptide molecules have also been identified as ligands to be used on affinity chromatography columns. The identification, isolation and synthesis of binding peptide molecules capable of binding factor VIII and/or factor VIII-like polypeptides are disclosed in U.S. Pat. No. 6,197,526. A phage display method is disclosed that is useful for identifying families of polypeptide binding molecules. Using the disclosed method, several binding peptides exhibiting high affinity for factor VIII and factor VIII-like peptides were identified and isolated. The identified peptides were shown to bind REFACTO®. The disclosures of U.S. Pat. No. 6,197,526 are incorporated by reference herein in their entirety.

In Toole et al., *Exploration of Structure-Function Relationships in Human Factor VIII by Site-Directed Mutagenesis*, Cold Spring Harbor Symposium on Quantitative Biology, 51:543 (1986) it was reported that recombinant FVIII could be purified by a combination of monoclonal antibody or peptide ligand affinity chromatography and ion-exchange chromatography. U.S. Pat. No. 5,470,954 describes a similar process in which FVIII is passed directly from immunoaffinity purification to the ion exchange column. In that document, it is stated that changing the ionic strength or polarity of the eluted polypeptide solution increases the chance that monoclonal antibodies will remain bound to the FVIII polypeptide and co-purify.

U.S. Pat. No. 6,683,159 describes methods for purification of Factor VIII polypeptides by affinity chromatography and ion exchange chromatography. The disclosed method includes the step of diluting the elution solution with a solution comprising higher ionic strength than that of the elution solution, resulting in a diluted Factor VIII solution. In an alternate embodiment, an elution solution is used that has a lower concentration of non-polar agent than that of the desorbing solution. The methods disclosed therein resulted in improved purification without significant yield loss. The disclosure of U.S. Pat. No. 6,683,159 is hereby incorporated by reference in its entirety.

SUMMARY OF THE INVENTION

In the present invention, it has been found that diluting the eluate from the monoclonal antibody or peptide ligand column provides certain advantages in processing time and/or reduced monoclonal antibody contamination of the FVIII protein being purified therefrom. In addition, it has been found that adding a salt to the eluate or the diluted eluate will increase recovery of FVIII protein. Accordingly, the present invention provides improved methods for the purification of procoagulant proteins, including both FVIII and variants thereof, which may be produced by recombinant techniques in higher yield and/or in more homogeneous form.

The present invention provides improved methods of purification of VIII protein from cell cultures, preferably from recombinant cell cultures. The methods provide for obtaining FVIII protein of a higher purity than methods currently in use. In one embodiment, the methods of the present invention comprise diluting the eluate from the immunoaffinity column with a solution of higher ionic strength than the eluate solution. In another embodiment, the methods of the present invention comprise diluting the eluate from an affinity column with a solution containing lower amounts of ethylene glycol than contained in the eluate solution. A further embodiment is a method wherein a salt, in particular NaCl, is added to the eluate or diluted eluate to increase recovery.

DETAILED DESCRIPTION OF THE INVENTION

The original manufacturing process for Factor VIII peptides uses a monoclonal antibody (Mab) affinity step, which provides excellent removal of process-related impurities such as DNA and host cell proteins (Eriksson et al., *Sem Hematol*, 38 (Suppl 4): 24-31, 2001). However, replacement of the Mab step with a peptide ligand could confer additional process benefits, including higher column loading capacities, improved resin cleaning afforded by a broader sanitization solution compatibility, and cost reduction in raw materials. Most importantly, however, the peptide can be chemically synthesized, eliminating the requirement for a Mab derived from murine hybridomas. Substitution of a chemically-synthesized ligand for the Mab eliminates any potential for introduction of an adventitious virus into the FVIII product stream, such as infectious retroviruses known to be associated with hybridoma cultures (Adamson, *Dev Biol Stand* 93:89-96, 1998; Bartal et al., *Med Microbiol Immunol* [Berl] 174: 325-332, 1986; Machala et al. *Folia Biol* [Praha] 32:187-182, 1986). A virus removal filtration step may also be incorporated into the process to provide the greatest possible degree of assurance that the VIII product and similarly other peptides having factor VIII activity are free of adventitious viral contaminants.

The use of peptide ligands in affinity chromatography of Factor VIII is described in Kelley et al, *Biotechnology and Bioengineering*, 87(3):400-412 (2004), and Kelley et al, *Journal of Chromatography A*, 1038:121-130 (2004), the disclosures of which are incorporated by reference herein in their entirety. As shown in these publications, phage display technology can lead to the rapid identification of affinity ligands that are particularly well suited for chromatographic use. In addition, the peptide can incorporate beneficial design elements, for example, confer resistance to chemicals used for cleaning the resin, allow for directed immobilization, or provide spacers to overcome steric hindrance.

Accordingly, the present invention provides improved methods for purification of a Factor VIII polypeptide comprising:
  a) adding a mixture containing Factor VIII polypeptide to be purified to an affinity matrix which binds by hydrophobic and/or electrostatic and/or van der Waals attractions to the FVIII polypeptide;

b) eluting the Factor VIII polypeptide from the affinity matrix with an elution solution that causes desorption of the Factor VIII polypeptide;

c) diluting the elution solution with a solution comprising higher ionic strength than that of the elution solution, resulting in a diluted Factor VIII solution;

d) passing the diluted Factor VIII solution through an ion exchange column capable of binding to the Factor VIII polypeptide, thereby binding the Factor VIII polypeptide while allowing contaminants to pass through the ion exchange column; and e) eluting the purified Factor VIII polypeptide from the ion exchange column.

The elution solution of step (b) may contain no salt, or alternatively, salt may be added to the solution. The dilution of step (c) is preferably performed using a solution comprising from about 5 to about 20 mM NaCl, preferably about 7 to about 20 mM NaCl, most preferably about 7 to 15 mM. The eluting solution is preferably diluted with salt-containing solution from about 3-fold to about 5-fold, most preferably about 3-fold. If salt is added in either step (b) or (c), the eluting solution should preferably be diluted in step (c) such that the salt is present at about 5 to about 20 mM NaCl, preferably about 7 to about 15 mM NaCl.

In a preferred embodiment, in step (b) of the method of the present invention the elution solution of step (b) comprises a non-polar agent. Any non-polar agent may be used, such as ethylene glycol, dioxane, propylene glycol and polyethylene glycol, or any appropriate low ionic strength, low polarity buffered solution. Preferably, the elution solution of step (b) contains ethylene glycol, more preferably about 50% (v/v) ethylene glycol.

Optionally, the elution solution may also contain a salt, e.g., NaCl, in a range of 1-50 mM, preferably 5-30 mM, more preferably 7-20 mM, and most preferably 10-15 mM. If the elution solution contains about 7-20 mM of salt, the dilution step (c) may be eliminated.

The dilution of step (c) is performed using a solution comprising less than about 50% (v/v) ethylene glycol, such that the final concentration of ethylene glycol is from about 17% to about 33% (v/v). In a preferred embodiment, the elution solution of step (b) contains 50% (v/v) ethylene glycol, and the dilution of step (c) is performed using a solution comprising no ethylene glycol, such that the final concentration of ethylene glycol is from about 17 to about 33% (v/v), most preferably about 33% (v/v) ethylene glycol. Preferably, the elution solution is diluted from about 1.5-fold to about 3-fold, most preferably about 1.5 fold, or 2:3.

The Factor VIII polypeptide of the present invention is generally produced recombinantly, but may also be purified from plasma. The recombinant Factor VIII polypeptide may be natural full length Factor VIII polypeptide, or a variant, such as a B-domain deleted variant of Factor VIII, including the VIII:SQ variant.

In preferred embodiments, the mixtures containing Factor VIII polypeptides may also include detergents and/or solvents, such as polyoxyethyl detergents, including Triton X-100, Tween 80. In addition, the Factor VIII polypeptide containing solution may include buffering substances, such as histidine. Salts, e.g., $CaCl_2$ and NaCl, may also be present.

Standard columns and resins known in the art may be used in the methods of the invention. Chromatographic columns ranging in diameter of 0.5-2.5 cm and about 10 cm in height are particularly useful. The affinity column useful in the present invention may be any industrially acceptable column and resin to which is adsorbed one or more monoclonal antibody or peptide ligands, which antibodies or ligands are capable of binding to a Factor VIII polypeptide and from which the Factor VIII polypeptide may later be released using standard methods and reagents. Standard resins known in the art may be used. For example, NHS Sepharose 4 FF from Amersham Biosciences (Arlington Heights, Ill.) may be used.

The affinity chromatography resin is produced by a coupling reaction that employs a commercially-available pre-activated base matrix, and is validated with a robust and scalable coupling process. Onto the resin is loaded a molecule that will bind by hydrophobic and/or electrostatic and/or van der Waals attractions to the FVIII polypeptide. Examples of such molecules are monoclonal antibodies (mAb), peptide ligands and triazine dyes. The molecule is selected under conditions used for affinity purification of Factor VIII. The columns may be loaded using art-recognized conditions. For example, a column may preferably be loaded at moderate flowrate (about 60 cm/h) with 10-25 column volumes of load.

Suitable monoclonal antibodies, for example, are disclosed in Fass et al., *Blood,* 59:594-600 (1982). This description is incorporated by reference in its entirety.

Suitable peptide ligands, for example, are disclosed in U.S. Pat. Nos. 6,197,526 and 6,492,105. The descriptions of these antibodies and ligands are incorporated by reference herein in their entirety. Kelley et al, *Biotechnology & Bioengineering,* discloses that a TN8.2 peptide ligand was identified by screening a bacteriophage display library. The peptides were designed to have between seven and ten residues between cysteine residues that oxidize to form a disulfide bond, and hence a constrained ring. See, e.g., FIG. 2 of Kelley et al. The peptide ligands can be immobilized on the columns using amine, hydroxyl, carboxylate or hydrazine groups. Sundaram et al, "Affinity Separation," in Stephanopolous G. (ed.) *Biotechnology, vol.* 3. *Bioprocessing.* New York: VCH, p 643-677.

The peptide ligands can be chemically synthesized, identified by phage display techniques. The peptide contains a disulfide bond-constrained loop that interacts with Factor VIII preferably in a single site on the light chain. Preferably, the peptide binds to Factor VIII with a dissociation constant of about 0.1 to about 10 µM, more preferably about 1 µM, both in free solution and when immobilized on a chromatographic resin. Suitable peptides are described, for example, in U.S. Pat. No. 6,197,526. The description of the peptides and how to obtain and use such peptides is hereby incorporated by reference in its entirety.

The peptide ligand allows a relatively simple substitution of the peptide affinity resin for the monoclonal antibody resin. See, Kelly et al and Kelley et al, supra. However, it should be noted that Factor VIII may bind differently to a monoclonal antibody resin than to a peptide ligand resin. For example, Factor VIII may bind through the light chain to a monoclonal antibody resin and through the heavy chain to a peptide ligand resin.

Examples of triazine dyes that may be used to purify a Factor VIII polypeptide include those well known in the art. ProMetic Biosciences, for example, has columns with triazine dyes.

The present invention will now be described in terms of the following non-limiting examples.

EXAMPLE 1

Preparation of Recombinant Factor VIII:SQ

The production of recombinant factor VIII:SQ (r-VIII SQ) was essentially performed as described in patent WO-A-

9109122. A DHFR deficient CHO cell line (DG44NY) was electroporated with an expression vector containing the r-VIII SQ gene and an expression vector containing the dihydrofolate reductase gene. The conditioned medium (containing fetal calf serum) was clarified and then concentrated by tangential flow filtration. The solution was loaded onto an SP Sepharose Fast Flow cation exchange resin, wherein the r-VIII SQ binds selectively to the resin through electrostatic forces.

The r-VIII SQ was eluted from the column at elevated ionic strength by flowing elution solution (0.8 M NaCl, 3 mM EDTA, 0.02% (v/v) surfactant [Octoxynol 9], 0.1 $MNH_4Ac$, 5 mM $CaCl_2$, 1M Sorbitol, pH 6.3±0.2) and was collected as a single UV adsorbing peak. The r-VIII SQ was then put through a virus inactivation step employing the solvent/detergent method using TNBP [Tri-(n-butyl)phosphate] and surfactant [such as Octoxynol 9, Triton X-100].

The r-VIII SQ was next loaded onto an affinity chromatography gel, where the ligand is a monoclonal antibody (mAb, named 8A4) directed towards the heavy chain of factor VIII. After washing, the factor VIII was eluted with a buffer containing 0.05 M histidine, 0.05 M $CaCl_2$ and 50% ethylene glycol and 0.02% Octoxynol 9 (Tween), pH 6.6. The mAb eluate was loaded onto an anion exchange column, Q Sepharose® FF sold by Pharmacia AB of Uppsala, Sweden. After washing, the FVIII SQ was eluted with a Q elution buffer containing 0.05 M histidine, 4 mM $CaCl_2$ 0.4 M NaCl, pH 6.3.

In order to improve upon the above purification system, several series of experiments were conducted to evaluate the effects on FVIII recovery of (a) dilution; (b) dilution with added NaCl; and (c) dilution with reduced, or with no, ethylene glycol.

Q Equilibration Buffer

The solution used to equilibrate the Q-column (the same as the desorption buffer of the monoclonal antibody column) prior to loading onto the ion exchange column comprises approximately the following composition:

0.05 M histidine
0.05 M calcium chloride
50% (v/v) ethylene glycol
0.02% (v/v) Octoxynol 9 or other surfactant
pH 6.6±0.2

Series 1: Dilution with Q Equilibration Buffer

Following affinity purification, the eluate was diluted from about 3-fold to about 5-fold with Q-equilibration buffer. In the 3-fold dilution, total recovery of FVIII activity was acceptable, though reduced, while murine IgG detected in the eluate was very low. At higher dilutions, the loss of yield of FVIII activity was significant.

Series 2: Dilution with Q Equilibration Buffer Containing NaCl

Following affinity purification, the eluate was diluted from about 3-fold to about 5-fold with Q-equilibration buffer containing NaCl in the range of about 7 to about 20 mM. Dilution generally produces a significant reduction in the amount of murine IgG across the ion exchange column. Surprisingly, the addition of NaCl also increased recovery of FVIII activity. This increase in recovery was sufficient to offset the loss in recovery resulting from dilution. The best results were observed in 3-fold to 5-fold dilutions with NaCl in the range of about 10 to about 17 mM NaCl. The best recovery yields of FVIII activity were obtained with dilutions of about 3-fold with about 15 mM NaCl. Dilution with less than about 7 mM NaCl or greater than about 20 mM NaCl resulted in a loss of final recovery of FVIII activity.

The conclusion is that addition of about 7 mM to about 20 mM NaCl to the Q Equilibration Buffer used to dilute the affinity eluate restores the loss of yield associated with dilution without NaCl, while also producing beneficial results by reducing the murine antibody detected in the eluate. In the most preferred embodiment, addition of Q Equilibrium Buffer with about 15 mM NaCl added produced optimal results.

Series 3 and 4: Dilution with Q Equilibration Buffer with No or Reduced Ethylene Glycol Following affinity purification, the eluate was diluted from about 1.5-fold to about 3-fold with Q Equilibration Buffer that does not contain ethylene glycol, resulting in final ethylene glycol content varying from about 50% (v/v) in the Q Equilibration Buffer down to as low as about 17% (v/v) in the 3-fold dilution without ethylene glycol. A 1.5-fold dilution without ethylene glycol resulted in about a 33% (v/v) final ethylene glycol concentration. With decreased ethylene glycol concentration, total recovery of protein increased over comparable dilution with Q Equilibration Buffer containing about 50% (v/v) ethylene glycol.

EXAMPLE 2

Introduction

A suitable downstream purification process for Factor VII-I:SQ as produced in Example 1 may consist of five chromatographic steps: cationic exchange (SP Sepharose FF), immunoaffinity (mAb Sepharose FF), anionic exchange (Q Sepharose FF), hydrophobic interaction (HIC, butyl Sepharose FF), and gel permeation chromatography (Superdex 200 pg). The eluate from the mAb column may be directly loaded onto a Q-Sepharose FF column. A series of loading conditions on Q-Sepharose FF column was examined by PPD (in collaboration with P&U, Stockholm) to (i) study the impact of the loading conditions on the activity recovery and the reduction in mouse IgG and HCP levels in the Q-Sepharose peak pool; and (ii) establish optimal loading conditions on the anion exchanger. Results of this study are summarized in this Example.

Experimental Procedures

Material

Q-Sepharose FF resin was packed in a 79×5 mm ID Pharmacia HR column. All buffers employed in this study were prepared by CTS by established procedures. The mAb peak pool from the purification process was obtained frozen at −80° C. from P&U, Stockholm (LtE 923). The COBAS assay kit and mega standard was bought from Chromogenix AB, Sweden.

Procedures

Q-Sepharose Scale Down Runs:

The Q-Sepharose FF column was initially equilibrated with 10 CV of buffer at a flow rate of 0.5 ml/min. Subsequently, the mAb peak pool was diluted with the appropriate dilution buffer and loaded onto the Q-Sepharose FF column at a flow rate of 0.2 ml/min. The total activity units loaded in all the experiments was 48,350 U/ml of the resin, and is close to the upper limit specified in the PLA. The activity of the mAb peak pool used to perform these experiments was 2860 IU/ml. The load volume in the 3-fold and 5-fold dilution experiments was, therefore, 78.6 mls and 131 mls respectively. Following the load, the column was washed with 40 CVs of a buffer containing 150 mM NaCl, 4 mM CaCl$_2$, 50 mM Histidine, pH 6.6, at a flow rate of 0.32 ml/min (wash 2). The bound protein was then eluted with a buffer containing 400 mM NaCl, 4 mM CaCl$_2$, 50 mM Histidine, pH 6.3 at a flow rate of 0.05 ml/min. Wash 2 and elution in all the experiments were performed at a flow rate of 0.05 ml/min. Wash 2 and elution in all the experiments were performed in the reverse direction. The column effluent during the various operations was collected and assayed for activity. A 1.6 cv fraction was pooled during elution beginning at the upward drift in the absorbance at 280 nm and is termed the peak pool. The load and peak pool samples were assayed for mouse IgG and HCP levels by performing ELISA (P&U, Stockholm).

Time Course Stability Studies:

The mAB peak pool was diluted different fold with (i) mAb elution buffer and (ii) mAb elution buffer containing 40 mM NaCl, and incubated at room temperature. The activity in these samples was then assayed at different time points.

Results and Discussions

Time Course Stability Study:

The mAB peak pool was diluted 2-fold, 3-fold and 5-fold with mAB elution buffer and incubated at room temperature. The drop in activity of these samples was monitored as a function of time. A modest drop of 20% in activity was observed over the course of 24 hours. The loss in activity was negligible at the end of 4 hours, and less than 10% at the end of 8 hours. Further, percentage drop in activity was observed to be independent of the extent of dilution of the mAb peak pool and hence independent of the solution concentration of FVIII in the mAb elution buffer. Similar results were obtained upon dilution of the mAb peak pool with mAb elution buffer containing 40 mM NaCl.

Q-Sepharose Scale Down Experiments:

Results from the scale-down runs of the Q-Sepharose FF column performed with the mAb peak pool diluted 3-fold and 5-fold with the mAb elution buffer are shown in Table 1.

TABLE 1

Dilution with mAb Elution Buffer

| Dilution Fold | Challenge (IU/ml resin) | Load (IU/ml) | Loading Time (hours) | Load Activity at End of Run (% of Initial Activity) | Flow Through Loss (%) |
|---|---|---|---|---|---|
| 3 | 48,350 | 953 | 6.55 | 82.8 | 3.6 |
| 5 | 48,350 | 572 | 10.9 | 70.4 | 3.3 |

| Dilution Fold | Wash #1 (%) | Wash #2 (%) | Pre-Peak (%) | Peak (1.6 cv) (%) | Post-Peak (%) | Total Recovery |
|---|---|---|---|---|---|---|
| 3 | 0.7 | 0.1 | <0.1 | 57.4 | 3.9 | 65.8 |
|   | 0.4 | 0.1 | <0.1 | 41.3 | 2.5 | 47.7 |

The flow-through losses in both cases were approximately 3.5% of the load, while the combined activity losses in the wash and prepeak samples were less then 1%. The activity in the 1.6 cv peak pool for the 3- and 5-fold dilution experiments were 57.5% and 41.3%, respectively, of the load, while the post-peak accounted for 3.9 and 2.5% of the load activity units, respectively. The corresponding values in manufacturing runs, wherein the mAb peak pool was loaded onto the column with no further modification of the eluate, was 5% in the flow-through and 70±9% in the peak pool. The other effluent streams have negligible activity.

These results clearly demonstrate that the yield across the Q-Sepharose FF column is sensitive to the extent of dilution of the mAb peak pool prior to loading onto the column, and decreases with increasing dilution. For a fixed number of activity units loaded onto the column, the operating time increases with dilution. As suggested by the time course stability data, a drop in yield can therefore be expected at higher load dilutions. Nevertheless, experimentally obtained activity values from the scale down runs was significantly lower than supported by the time course stability data. One possible explanation is that the adsorption of FVIII:SQ onto the Q-Sepharose resin under dilute conditions leads to stronger interaction with the resin and has a denaturing effect on the protein, thereby leading to a lower recovery upon elution. The yield at higher dilutions could then be improved by attenuating the 'FVIII:SQ-resin' interaction during loading. In order to test this hypothesis, subsequent experiments were performed with the mAb peak pool diluted with mAb elution buffer containing NaCl.

Dilution with mAb Elution Buffer Containing NaCl:

The results from the Q-Sepharose scale down experiments performed using mAb peak pool diluted with mAb elution buffer containing various concentrations of NaCl is shown in Table 2.

TABLE 2a

5-Fold Dilution With mAb Elution Buffer Containing NaCl

| Load NaCl Conc. (mM) | Challenge (IU/ml resin) | Load (IU/ml) | Loading Time (hours) | Load Activity at End of Run (% of Initial Activity) | Flow Through Loss (%) |
|---|---|---|---|---|---|
| 10 | 48,350 | 572 | 10.9 | 90.3 | 6.5 |
| 10 | 48,350 | 572 | 10.9 | 85.8 | 6.8 |
| 15 | 48,350 | 572 | 10.9 | 76.4 | 6.6 |
| 20 | 48,350 | 572 | 10.9 | 73.3 | 6.9 |
| 20 | 48,350 | 572 | 10.9 | 88.9 | 8.5 |

| Load NaCl Conc. | Wash #1 (%) | Wash #2 (%) | Pre-Peak (%) | Peak (1.6 cv) (%) | Pos-Peak (%) | Total Recovery |
|---|---|---|---|---|---|---|
| 10 | 0.8 | 0.2 | <0.1 | 73.1 | 1.8 | 82.4 |
| 10 | 0.9 | 0.2 | <0.1 | 71.8 | 3.4 | 83.1 |
| 15 | 0.9 | 0.1 | — | 61.0 | 7.3 | 75.9 |
| 20 | 0.9 | 0.2 | — | 49.8 | 12.4 | 70.3 |
| 20 | 1.0 | 0.2 | — | 46.3 | 20.1 | 76.1 |

TABLE 2b

3-Fold Dilution With mAb Elution Buffer Containing NaCl

| Load NaCl Conc. (mM) | Challenge (IU/ml resin) | Load (IU/ml) | Loading Time (hours) | Load Activity at End of Run (% of Initial Activity) | Flow Through Loss (%) |
|---|---|---|---|---|---|
| 7 | 48,350 | 953 | 6.55 | 94.4 | 5.5 |
| 10 | 48,350 | 953 | 6.55 | 86.3 | 6.0 |
| 12.5 | 48,350 | 953 | 6.55 | 91.6 | 9.1 |
| 16.7 | 48,350 | 953 | 6.55 | 82.0 | 6.5 |

| Load NaCl Conc. | Wash #1 (%) | Wash #2 (%) | Pre-Peak (%) | Peak (1.6 cv) (%) | Post-Peak (%) | Total Recovery |
|---|---|---|---|---|---|---|
| 7 | 1.3 | 0.1 | — | 58.3 | 9.9 | 75.1 |
| 10 | 1.3 | 0.1 | — | 79.9 | 3.2 | 90.5 |
| 12.5 | 2.1 | 0.6 | — | 58.8 | 12.0 | 82.5 |
| 16.7 | 1.7 | 0.4 | — | 59.3 | 4.7 | 72.6 |

5-Fold Dilution Experiments:

Loading the diluted mAb peak pool under conditions that attenuate the 'FVIII:SQ-resin' interaction significantly increased the overall activity recovery across the Q-Sepharose column. A greater fraction of this increase in activity was seen in the peak pool for the runs employing 10 and 15 mM NaCl in the load, suggesting that there exists an optimal NaCl concentration that leads to a maximum peak activity recovery.

In the NaCl concentration range of about 7 to 20 mM, the activity loss in the flow through varied between 6.5 and 8.5%. These values are twice of that seen in the 5-fold dilution run in the absence of NaCl. The combined wash and prepeak activity losses in all cases were less than 2%. The activity losses in the post-peak pool increases with increasing NaCl concentration and was as high as 20% at an NaCl concentration of 20 mM. This is expected since the protein migrates farther down the column during loading and subsequently takes longer to elute when the flow is reversed.

3-Fold Dilution:

As in the case of 5-fold dilution, the overall activity recovery and flow-through losses were higher when loaded in the presence of NaCl. The maximum overall and peak activity recovery was obtained at a NaCl concentration of 15 mM. However, existence of an optimum NaCl concentration is not as evident at this dilution level as it was at 5-fold dilution.

Mouse IgG Results:

The mouse IgG data on the peak and post-peak pools for all 3- and 5-fold dilution experiments are shown in Table 3:

TABLE 3

Mouse IgG Data from 3-Fold and 5-Fold Dilution Experiments

| Dilution Fold | Load NaCl Concentration | IgG Levels in Peak Pool (ng/KIU) | IgG Levels in Post-Peak Pool (ng/KIU) |
|---|---|---|---|
| 3-fold | 0 | 0.8 | 2.1 |
|  | 7 | 0.5 | 2.0 |
|  | 10 | 0.8 | 5.3 |
|  | 12.5 | 0.7 | 1.8 |
|  | 16.7 | 1.2 | 3.6 |
| 5-fold | 0 | 0.5 | 2.1 |
|  | 10 | 0.8 | 3.2 |
|  | 10 | 0.8 | 3.6 |
|  | 15 | 0.7 | 2.3 |
|  | 20 | 0.4 | 1.5 |
|  | 20 | 0.6 | 1.3 |

The IgG values in the peak pool for the 3-fold dilution runs varied from 0.5 to 1.2 ng/KIU for the 5-fold dilution runs. The corresponding values in manufacturing runs, wherein the mAb peak pool was loaded onto the column with no further modification of the elute, averaged 2.3 ng/KIU. Thus, dilution of the mAb peak pool with mAb elution buffer, with or without NaCl, prior to loading reduced the IgG levels in the Q-Sepharose peak pool. This effect, beyond the mere dilution of IgG levels, may be the result of a given association constant for formation of IgG-FVIII:SQ complex. Thus, lowering the concentrations of the IgG and FVIII:SQ lowers the concentration of the complex, thereby allowing greater removal of IgG across the ion exchanger. In both the 3-fold and 5-fold dilution experiments, no correlation was observed between IgG values in the Q-Sepharose peak pool and NaCl concentrations in the load. Thus, in the range of NaCl concentrations employed in these experiments, addition of NaCl does not appear to provide additional reduction in mouse IgG levels.

Host Cell Protein Results:

The host cell protein data on the peak pool for the 3-fold and 5-fold dilution experiments are shown in Table 4:

TABLE 4

Host Cell Protein (HCP) Levels in 3-Fold and 5-Fold Dilution Experiments

| Dilution Fold | Load NaCl Conc (mM) | HCP in Peak Pool (ng/KIU |
|---|---|---|
| 3 | 7 | 10.3 |
|  | 12.5 | 4.2 |
| 5 | 10 | 14.1 |
|  | 15 | 9.9 |
|  | 20 | 10.9 |

The corresponding values in manufacturing runs, wherein the mAb peak pool is loaded onto the column with no further modification of the eluate, averaged 20 ng/KIU. These results suggest that the HCP levels in the peak pool decrease with increasing NaCl concentrations, and are independent of the extent of dilution. The addition of NaCl may attenuate the binding of HCP to the resin and, therefore, allow lower levels of HCP in the Q-Sepharose peak pool.

Conclusions

Dilution of the mAb peak pool with mAb elution buffer prior to loading on a Q-Sepharose column significantly decreased the yield across this step. The decrease in yield is an increasing function of the extent of dilution. However, the solution stability of FVIII is independent of the extent of dilution with mAb elution buffer, thereby suggesting that loading under dilute conditions leads to a stronger 'VIII-resin' interaction and has a denaturing effect on the protein. Addition of sodium chloride to the dilution buffer attenuates the 'FVIII-resin' interaction and increases the yield across the Q-Sepharose column. Increasing the NaCl concentrations, however, increases the flow-through and post-peak losses, and hence there exists an optimum NaCl concentration at which the yield losses are significantly offset. The optimum concentration for the 3-fold and 5-fold dilution runs appears to be in the 7 to 20 mM concentration, and more particularly about 15 mM.

Diluting the mAb peak pool with mAb elution buffer also reduced the IgG and HCP levels in the Q-Sepharose peak pool. In the concentration range of NaCl examined, HCP levels in the Q-Sepharose peak pool decreased with increasing NaCl concentrations in the load. Overall, a combination of dilution of the mAb peak pool and adding NaCl at concentrations of 7 to 20 mM resulted in improved purification without significant yield loss.

EXAMPLE 3

Introduction

Definition of Solutions and Operating Conditions

The process conditions developed for the TN8.2 Sepharose step were based on the preexisting immunoaffinity step, with modifications adopted to streamline the process or improve efficiency. Slight modifications to the load composition were incorporated based on optimization of the SP-Sepharose elution buffer, which had a lower sodium chloride concentration and no longer contained sorbitol (the binding of BDDrFVIII to TN8.2 is not affected by this small change in salt or the presence of sorbitol). Column wash volumes were decreased, with no observable effect on product purity.

The load solution containing solvent and detergent from the virus inactivation step is compatible for loading the column, which is pre-equilibrated in a buffer of similar composition. The TN8.2 Sepharose column is loaded at moderate flowrate (approximately 60 cm/hr) with 15-25 column volumes of load. The load is immediately followed with a wash buffer containing a reduced level of Triton X-100 and no solvent. This wash is followed by a buffer containing 1M NaCl in order to dissociate CHO proteins that may be bound through weak electrostatic interactions to the ligand or product. This wash also serves to remove excess light chains of BDDrFVIII that are produced during the cell culture process and are not removed prior to this step. In preparation for elution, the column is washed with a low ionic strength buffer, and then eluted with 50% ethylene glycol, in the same manner as the immunoaffinity column. The product elutes as a single peak collected from the start of UV rise for 1.5 column volumes. The column is then cleaned and regenerated using a low pH 6M guanidine HCl solution, and stored in dilute ethanol between runs for microbiological control.

Load Conditions

Load Composition

Like the monoclonal antibody, 8A4, used in the recombinant Factor VIII purification process of Example 1, the TN8.2 load composition consists of the SP Sepharose elution plus the solvent/detergent chemicals of the subsequent viral inactivation step. The TN8.2 ligand was originally screened for REFACTO® Albumin Free (AF) binding under the REFACTO® 8A4 mAb buffer conditions.

EXAMPLE 4

Elution Conditions

Buffer Excipients

The elution conditions were examined as a potential source of increased recovery. Earlier work had indicated that NaCl might play a role in stabilizing F:VIII activity. It was critical that any changes made to the elution would not affect the downstream Q Sepharose step. As an ion exchanger, it was necessary to keep the ionic strength of the Q Sepharose load low, and adding too much NaCl could inhibit binding of REFACTO® AF. A NaCl concentration of 10-20 mM was shown to provide some stabilization of REFACTO® AF in 50% ethylene glycol. 15 mM was chosen as the experimental TN8.2 elution NaCl concentration, in order to increase the chances of observing a benefit while still minimally affecting the Q Sepharose load conditions.

TABLE 5

TN8.2 loaded at 25,000 U/ml and 75,000 U/ml.
10 mL columns, +/−15 mM NaCl in Wash 3 and elution.

| Conditions | [NaCl] in Wash 3 & Elution (mM) | % Peak Recovery | Total Recovery |
|---|---|---|---|
| 25,000 U/ml load | 0 | 76 | 78 |
| 25,000 U/ml load | 15 | 100 | 102 |
| 75,000 U/ml load | 0 | 58 | 62 |
| 75,000 U/ml load | 15 | 99 | 102 |

Discussion

These conditions were tested using different batches of both REFACTO® and REFACTO® AF, and also run several times as part of a 1/40$^{th}$-scale train. All runs had elution recoveries of over 80%, most were over 90%. This profound increase in elution recovery was a remarkable breakthrough in TN8.2 development. Furthermore, product purity and quality are not compromised with increased recovery. The DNA and CHO values, as well as for the 1/40$^{th}$-scale runs, were as good or better than those achieved on the 8A4 mAb.

Following the foregoing description, the characteristics important for purification of Factor VIII polypeptides by affinity chromatography and ion exchange chromatography can be appreciated. Additional embodiments of the invention and alternative methods adapted to a particular solution or feed stream will be evident from studying the foregoing description. All such embodiments and obvious alternatives are intended to be within the scope of this invention as defined by the claims that follow.

What is claimed is:

1. A method for purification of a Factor VIII polypeptide comprising:
   (a) adding a mixture containing a Factor VIII polypeptide to be purified to an affinity matrix which binds the Factor VIII polypeptide by hydrophobic and/or electrostatic and/or van der Waals attractions;
   (b) eluting the Factor VIII polypeptide from the affinity matrix with an elution solution which desorbs the Factor VIII polypeptide;
   (c) diluting the elution solution about 3-fold to about 5-fold with a solution comprising higher salt concentration than that of the elution solution, resulting in a diluted Factor VIII solution comprising about 7 to about 20 mM of a salt;
   (d) passing the diluted Factor VIII solution through an ion exchange column which binds the Factor VIII polypeptide, thereby allowing contaminants to pass through the ion exchange column; and
   (e) eluting the purified factor VIII polypeptide from the ion exchange column.

2. The method of claim 1, wherein the affinity matrix comprises a monoclonal antibody or peptide ligand.

3. The method of claim 2, wherein the affinity matrix comprises a monoclonal antibody.

4. The method of claim 2, wherein the affinity matrix comprises a peptide ligand.

5. The method of claim 4, wherein the peptide ligand is TN 8.2.

6. The method of claim 1, wherein a salt is added to the elution solution of step (b).

7. The method of claim 6, wherein the salt is NaCl.

8. The method of claim 1, wherein a salt is added to the diluted Factor VIII solution in step (c).

9. The method of claim 8, wherein the salt is NaCl.

10. The method of claim 8, wherein the elution solution of step (b) comprises no NaCl salt, and the diluted Factor VIII solution in step (c) comprises about 15 mM NaCl.

11. The method of claim 1, wherein the elution solution of step (b) comprises NaCl salt, and the diluted Factor VIII solution in step (c) comprises about 15 mM NaCl.

12. The method of claim 1, wherein the elution solution is diluted about 3-fold.

13. The method of claim 1, wherein the affinity matrix comprises monoclonal antibody, peptide ligand or triazine dye.

14. The method of claim 1, wherein the elution solution comprises ethylene glycol.

15. The method of claim 14, wherein the solution used to dilute the elution solution in step (c) comprises ethylene glycol.

16. A method for purification of a Factor VIII polypeptide comprising:
(a) adding a mixture containing a Factor VIII polypeptide to be purified to an affinity matrix which binds the Factor VIII polypeptide by hydrophobic and/or electrostatic and/or van der Waals attractions;
(b) eluting the Factor VIII polypeptide from the affinity matrix with an elution solution which desorbs the Factor VIII polypeptide, wherein the elution solution comprises at least one of ethylene glycol, dioxane, propylene glycol and polyethylene glycol;
(c) diluting the elution solution about 1.5-fold to about 3-fold with a solution comprising lower concentration of the ethylene glycol, dioxane, propylene glycol and/or polyethylene glycol than that of the elution solution, resulting in a diluted Factor VIII solution comprising about 17% to about 33% (v/v) ethylene glycol, dioxane, propylene glycol and/or polyethylene glycol;
(d) passing the diluted Factor VIII solution through an ion exchange column which binds the Factor VIII polypeptide, thereby allowing contaminants to pass through the ion exchange column; and
(e) eluting the purified Factor VIII polypeptide from the ion exchange column.

17. The method of claim 16, wherein the affinity matrix comprises a monoclonal antibody or peptide ligand.

18. The method of claim 17, wherein the affinity matrix comprises a monoclonal antibody.

19. The method of claim 17, wherein the affinity matrix comprises a peptide ligand.

20. The method of claim 19, wherein the peptide ligand is TN 8.2.

21. The method of claim 16, wherein the elution solution of step (b) comprises 50% (v/v) ethylene glycol, and the dilution of step (c) is performed using a solution comprising less than 50% (v/v) ethylene glycol, such that the final concentration of ethylene glycol in the diluted factor VIII solution is from about 17% to about 33% (v/v).

22. The method of claim 16, wherein the elution solution of step (b) contains 50% (v/v) ethylene glycol, and the dilution of step (c) is performed using a solution comprising no ethylene glycol, such that the final concentration of ethylene glycol in the diluted factor VIII solution is from about 17% to about 33% (v/v).

23. The method of claim 16, wherein the elution solution is diluted about 1.5-fold.

24. The method of claim 16, wherein a salt is added to the elution solution of step (b).

25. The method of claim 24, wherein the salt is NaCl.

26. The method of claim 16, wherein a salt is added to the diluted Factor VIII solution in step (c).

27. The method of claim 26, wherein the salt is NaCl.

28. The method of claim 16, wherein the elution solution of step (b) comprises no NaCl salt, and the diluted Factor VIII solution in step (c) comprises about 15 mM NaCl.

29. The method of claim 16, wherein the elution solution of step (b) comprises NaCl salt, and the diluted Factor VIII solution in step (c) comprises about 15 mM NaCl.

30. The method of claim 16, wherein the affinity matrix comprises monoclonal antibody, peptide ligand or triazine dye.

31. The method of claim 16, wherein the elution solution comprises ethylene glycol.

32. The method of claim 31, wherein the solution used to dilute the elution solution in step (c) comprises ethylene glycol.

33. A method for purification of a Factor VIII polypeptide comprising:
(a) adding a mixture containing a Factor VIII polypeptide to be purified to an affinity matrix which binds to the Factor VIII polypeptide;
(b) eluting the Factor VIII polypeptide from the affinity matrix with an elution solution which desorbs the Factor VIII polypeptide, wherein the elution solution comprises at least one of ethylene glycol, dioxane, propylene glycol and polyethylene glycol and a buffer;
(c) diluting the elution solution about 1.5-fold to about 3-fold with a solution comprising a lower concentration of the ethylene glycol, dioxane, propylene glycol and/or polyethylene glycol than that of the elution solution, resulting in a diluted Factor VIII solution comprising about 17% to about 33% (v/v) ethylene glycol, dioxane, propylene glycol and/or polyethylene glycol;
(d) passing the diluted Factor VIII solution through an ion exchange column which binds the Factor VIII polypeptide, thereby allowing contaminants to pass through the ion exchange column; and
(e) eluting the purified Factor VIII polypeptide from the ion exchange column.

34. The method of claim 33, wherein the affinity matrix comprises a monoclonal antibody or peptide ligand.

35. The method of claim 34, wherein the affinity matrix comprises a monoclonal antibody.

36. The method of claim 34, wherein the affinity matrix comprises a peptide ligand.

37. The method of claim 36, wherein the peptide ligand is TN 8.2.

38. The method of claim 33, wherein the elution solution of step (b) comprises no NaCl salt, and the diluted Factor VIII solution in step (c) comprises about 15 mM NaCl.

39. The method of claim 33, wherein the elution solution of step (b) comprises NaCl salt, and the diluted Factor VIII solution in step (c) comprises about 15 mM NaCl.

40. The method of claim 33, wherein the elution solution is diluted about 1.5-fold.

41. The method of claim 33, wherein a salt is added to the elution solution of step (b).

42. The method of claim 41, wherein the salt is NaCl.

43. The method of claim 33, wherein a salt is added to the diluted Factor VIII solution in step (c).

44. The method of claim 43, wherein the salt is NaCl.

45. The method of claim 33, wherein the affinity matrix comprises monoclonal antibody, peptide ligand or triazine dye.

46. The method of claim 33, wherein the elution solution comprises ethylene glycol.

47. The method of claim 46, wherein the solution used to dilute the elution solution in step (c) comprises ethylene glycol.

48. A method for purification of a Factor VIII polypeptide comprising:
(a) adding a mixture containing a Factor VIII polypeptide to be purified to an affinity matrix which binds the Factor VIII polypeptide by hydrophobic and/or electrostatic and/or van der Waals attractions;
(b) eluting the Factor VIII polypeptide from the affinity matrix with an elution solution which desorbs the Factor VIII polypeptide, wherein the elution solution comprises about 7 to about 20 mM of salt;
(c) passing the elution solution comprising Factor VIII solution through an ion exchange column which binds the Factor VIII polypeptide, thereby allowing contaminants to pass through the ion exchange column; and (d) eluting the purified factor VIII polypeptide from the ion exchange column.

49. The method of claim 48, wherein the elution solution of step (b) comprises about 15 mM NaCl.

50. The method of claim 48, wherein the affinity matrix comprises monoclonal antibody, peptide ligand or triazine dye.

51. The method of claim 48, wherein the elution solution comprises ethylene glycol.

52. A method for purification of a Factor VIII polypeptide comprising:
   (a) adding a mixture containing a Factor VIII polypeptide to be purified to an affinity matrix which binds the Factor VIII polypeptide by hydrophobic and/or electrostatic and/or van der Waals attractions;
   (b) eluting the Factor VIII polypeptide from the affinity matrix with an elution solution which desorbs the Factor VIII polypeptide, the elution solution comprising either a salt at a concentration of about 1 mM to about 25 mM or at least one of ethylene glycol, dioxane, propylene glycol and polyethylene glycol at a final concentration of about 50% (v/v);
   (c) diluting the elution solution about 3-fold to about 5-fold with a solution of higher ionic strength than that of the elution solution;
   (d) passing the diluted Factor VIII solution through an ion exchange column which binds the Factor VIII polypeptide, thereby allowing contaminants to pass through the ion exchange column; and
   (e) eluting the purified factor VIII polypeptide from the ion exchange column.

53. The method of claim 52, wherein the diluted Factor VIII solution comprises about 1 to about 50 mM of salt in step (c).

54. The method of claim 52, wherein the diluted Factor VIII solution comprises about 7 to about 20 mM of salt in step (c).

55. The method of claim 52, wherein the affinity matrix comprises monoclonal antibody, peptide ligand or triazine dye.

56. The method of claim 52, wherein the affinity matrix comprises monoclonal antibody or peptide ligand.

57. The method of claim 56, wherein the affinity matrix is a TN 8.2 peptide ligand.

58. The method of claim 52, wherein the elution solution comprises ethylene glycol.

59. The method of claim 58, wherein the solution used to dilute the elution solution in step (c) comprises ethylene glycol.

60. The method of claim 52, wherein the elution solution comprises a salt at a concentration of about 5 mM to about 20 mM.

61. The method of claim 60, wherein the elution solution comprises a salt at a concentration of about 5 mM, about 10 mM, about 15 mM, or about 20 mM.

62. The method of claim 52, wherein the final concentration of at least one of ethylene glycol, dioxane, propylene glycol and polyethylene glycol is about 17% to about 33% (v/v) in step (c).

* * * * *